United States Patent
Shute et al.

(10) Patent No.: US 11,311,244 B2
(45) Date of Patent: Apr. 26, 2022

(54) DEVICES AND METHODS FOR HEART SOUND DETECTION

(71) Applicant: Cardiac Pacemakers, Inc., St. Paul, MN (US)

(72) Inventors: Jonathan Bennett Shute, Minnetonka, MN (US); Bin Mi, Arden Hills, MN (US); Pramodsingh Hirasingh Thakur, Woodbury, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 627 days.

(21) Appl. No.: 16/113,438

(22) Filed: Aug. 27, 2018

(65) Prior Publication Data

US 2019/0083042 A1    Mar. 21, 2019

Related U.S. Application Data

(60) Provisional application No. 62/561,118, filed on Sep. 20, 2017.

(51) Int. Cl.
*A61B 5/00* (2006.01)
*A61B 7/04* (2006.01)
*A61N 1/37* (2006.01)

(52) U.S. Cl.
CPC .............. *A61B 5/7214* (2013.01); *A61B 7/04* (2013.01); *A61N 1/3702* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,951,678 A | * | 8/1990 | Joseph | A61B 7/023 600/484 |
| 7,424,321 B2 | * | 9/2008 | Wariar | A61B 7/00 600/514 |
| 2002/0151812 A1 | | 10/2002 | Scheiner et al. | |
| 2006/0270939 A1 | * | 11/2006 | Wariar | A61B 7/00 600/528 |
| 2011/0066041 A1 | * | 3/2011 | Pandia | A61B 5/318 600/484 |
| 2011/0105915 A1 | * | 5/2011 | Bauer | A61B 5/4806 600/484 |
| 2011/0313488 A1 | | 12/2011 | Hincapie Ordonez et al. | |

(Continued)

FOREIGN PATENT DOCUMENTS

CN   101862201 A    10/2010
CN   102688029 A    9/2012

(Continued)

OTHER PUBLICATIONS

"European Application Serial No. 18766463.6, Communication Pursuant to Article 94(3) EPC dated Jan. 11, 2021", 4 pgs.

(Continued)

*Primary Examiner* — Shirley X Jian
(74) *Attorney, Agent, or Firm* — Schwegman Lundberg & Woessner, P.A.

(57) ABSTRACT

This document discusses, among other things, systems and methods to produce a composite heart sound signal of a patient using a first signal including heart sound information over a first physiologic interval and a second signal including heart sound information over the first physiologic interval.

20 Claims, 6 Drawing Sheets

(56) References Cited

U.S. PATENT DOCUMENTS

| | | | |
|---|---|---|---|
| 2013/0109985 A1* | 5/2013 | Gillberg | A61B 5/7221 600/509 |
| 2014/0276163 A1 | 9/2014 | Thakur et al. | |
| 2017/0119273 A1 | 5/2017 | Thakur et al. | |
| 2018/0042499 A1* | 2/2018 | Sato | A61B 5/02125 |
| 2019/0125196 A1* | 5/2019 | Kline | A61B 5/7221 |

FOREIGN PATENT DOCUMENTS

| | | |
|---|---|---|
| CN | 105873499 A | 8/2016 |
| CN | 111107789 A | 5/2020 |
| WO | WO-2019060094 A1 | 3/2019 |

OTHER PUBLICATIONS

"European Application Serial No. 18766463.6, Response to Communication Pursuant to Rules 161 and 162 filed Oct. 28, 2020", 14 pgs.

"International Application Serial No. PCT/US2018/048103, International Preliminary Report on Patentability dated Apr. 2, 2020", 8 pgs.

"International Application Serial No. PCT/US2018/048103, International Search Report dated Dec. 14, 2018", 4 pgs.

"International Application Serial No. PCT/US2018/048103, Written Opinion dated Dec. 14, 2018", 8 pgs.

"European Application Serial No. 18766463.6, Response filed May 19, 21 to Communication Pursuant to Article 94(3) EPC dated Jan. 11, 2021", 12 pgs.

"Chinese Application Serial No. 201880060875.7, Office Action dated Dec. 23, 2021", w/o English translation, 10 pgs.

* cited by examiner

| | X | Y | Z |
|---|---|---|---|
| 1 | 1 | 0 | 0 |
| 2 | 0 | 1 | 0 |
| 3 | 0 | 0 | 1 |
| 4 | -1 | 1 | 0 |
| 5 | -1 | 0 | 1 |
| 6 | 0 | -1 | 1 |
| 7 | 1 | 1 | 0 |
| 8 | 1 | 0 | 1 |
| 9 | 0 | 1 | 1 |
| 10 | 1 | 1 | 1 |
| 11 | -1 | 1 | 1 |
| 12 | 1 | -1 | 1 |
| 13 | 1 | 1 | -1 |

FIG. 3

DEVICES AND METHODS FOR HEART SOUND DETECTION

CLAIM OF PRIORITY

This application claims the benefit of priority under 35 U.S.C. § 119(e) of U.S. Provisional Patent Application Ser. No. 62/561,118, filed on Sep. 20, 2017, which is herein incorporated by reference in its entirety.

TECHNICAL FIELD

This document relates generally to medical devices, and more particularly, but not by way of limitation, to systems, devices, and methods to detect heart sounds.

BACKGROUND

Implantable medical devices, such as cardiac rhythm management (CRM) devices, can be used to monitor, detect, and/or treat various cardiac conditions that can result in a reduced ability of a heart to sufficiently deliver blood to a body. In some cases, heart conditions may lead to rapid, irregular, or inefficient heart contractions. To alleviate one or more of these conditions, various medical devices can be implanted in a patient's body to monitor heart activity or to provide electrical stimulation to optimize or control contractions of the heart.

OVERVIEW

Traditional cardiac rhythm management (CRM) devices, such as pacemakers or defibrillators, include subcutaneous devices implanted in a chest of a patient, having one or more leads to position one or more electrodes or other sensors at various locations in the heart, such as in one or more of the atria or ventricles. In certain examples, the one or more leads can include a pressure sensor positioned in the heart and coupled to the CRM device through a conductor in the lead. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient.

For example, the CRM device or the one or more leads can include an acoustic sensor, such as an accelerometer, a microphone, or one or more other acoustic sensors configured to detect body sounds from a patient, such as cardiac murmurs, respiratory sounds, heart sounds, mitral regurgitation, mitral stenosis, or other body sounds. The body sounds, or other physiologic information, can be used to diagnose one or more physiologic conditions, provide an alert, or to control one or more therapies.

Leadless devices, such as implantable cardiac monitors, leadless cardiac pacemakers (LCP), insertable cardiac monitors (ICM), etc., and external devices, such as wearable remote patient monitors, etc., have developed that can detect physiologic information from, and in certain examples, provide one or more therapies or stimulation to the heart, without traditional lead or implantable CAM device complications. Such leadless and wearable devices are typically small, self-contained devices (e.g., smaller than traditional implantable CRM devices), in certain examples, having even more limited power and processing capabilities than a traditional CRM device.

This document discusses, among other things, apparatus, systems, and/or methods to produce a composite heart sound signal by using signals containing heart sound information. An example system can include a heart sound input circuit and a heart sound circuit. The heart sound input circuit can be configured to receive a first signal including heart sound information from a first axis over a first physiologic interval. The sound input circuit can also be configured to receive a second signal including heart sound information from a second axis over the first physiologic interval, where the first physiologic interval includes at least a portion of a cardiac cycle, and the first axis is different than the second axis. In an example, the first signal can include heart sound information from a first axis of an accelerometer, and the second signal can include heart sound information from a second axis of the accelerometer. In other examples, one or more other heart sound sensors can be used, or more than one heart sound sensor, including more than one accelerometer. In an example, the heart sound circuit can be configured to produce a composite heart sound signal over the first physiologic interval using the first and second signals.

An example (e.g., "Example 1") of subject matter (e.g., a system) may include a system comprising: a heart sound input circuit configured to: receive a first signal including heart sound information from a first axis over a first physiologic interval; and receive a second signal including heart sound information from a second axis over the first physiologic interval, the first physiologic interval including at least a portion of a cardiac cycle, the first axis different than the second axis; and a heart sound circuit configured to produce a composite heart sound signal over the first physiologic interval using the first and second signals.

In Example 2, the subject matter of Example 1 may optionally be configured such that the heart sound circuit is configured to correct the first signal over the first physiologic interval using the second signal over the first physiologic interval.

In Example 3, the subject matter of any one or more of Examples 1-2 may optionally be configured such that the heart sound circuit is configured to produce the composite heart sound signal using the first and second signals without reference to an electrical signal of the heart.

In Example 4, the subject matter of any one or more of Examples 1-3 may optionally be configured such that the heart sound input circuit is configured to receive a third signal including heart sound information from a third axis over the first physiologic interval, the third axis different than the first and second axes.

In Example 5, the subject matter of any one or more of Examples 1-4 may optionally be configured such that the heart sound circuit is configured to produce a plurality of potential composite heart sound signals as a function of the first and second signals and to produce the composite heart sound signal by selecting the potential composite heart sound signal using a signal-to-noise-ratio of the potential composite heart sound signals.

In Example 6, the subject matter of any one or more of Examples 1-5 may optionally be configured such that the heart sound circuit is configured to produce each of the potential composite heart sound signals by applying a plurality of first coefficients to the first signal, a plurality of second coefficients to the second signal, and a plurality of third coefficients to the third signal.

In Example 7, the subject matter of any one or more of Examples 1-6 may optionally be configured such that the heart sound circuit is configured to select the first and second coefficients using the first and second signals over the first physiologic interval, and wherein the heart sound circuit is configured to apply the selected first coefficient to the first signal and the second coefficient to the second signal to produce the composite heart sound signal over a second physiologic interval subsequent to the first physiologic interval.

In Example 8, the subject matter of any one or more of Examples 1-7 may optionally be configured such that the heart sound circuit is configured to store the first and second coefficients based on a condition sensed by the heart sound circuit, and is configured to apply the first and second coefficients when the condition is sensed again.

Example 9 is a method comprising: receiving a first signal including heart sound information from a first axis over a first physiologic interval using a heart sound input circuit: receiving a second signal including heart sound information from a second axis over the first physiologic interval, the first physiologic interval including at least a portion of a cardiac cycle, the first axis different than the second axis; and producing, using a heart sound circuit, a composite heart sound signal over the first physiologic interval using the first and second signals.

In Example 10, the subject matter of Example 9 may optionally be configured such that producing the composite heart sound signal includes correcting the first signal over the first physiologic interval using the second signal over the first physiologic interval.

In Example 11, the subject matter of any one or more of Examples 9-10 may optionally be configured such that producing the composite heart sound signal includes using the first and second signals without reference to an electrical signal of the heart.

In Example 12, the subject matter of any one or more of Examples 9-11 may optionally include receiving a third signal including heart sound information from a third axis over the first physiologic interval using the heart sound input circuit, the third axis different than the first and second axes.

In Example 13, the subject matter of any one or more of Examples 9-12 may optionally include producing, using the heart sound circuit, a plurality of potential composite heart sound signals using the first and second signals; wherein producing the composite heart sound signal includes selecting the potential composite heart sound signal using a signal-to-noise-ratio of the potential composite heart sound signals.

In Example 14, the subject matter of any one or more of Examples 9-13 may optionally include wherein producing each of the potential composite heart sound signals includes applying a plurality of first coefficients to the first signal, a plurality of second coefficients to the second signal, and a plurality of third coefficients to the third signal using the heart sound circuit.

In Example 15, the subject matter of any one or more of Examples 9-14 may optionally include selecting the first and second coefficients using the first and second signals over the first physiologic interval; and applying the selected first and second coefficients to the first signal and the second signal to produce the composite heart sound signal over a second physiologic interval subsequent to the first physiologic interval.

Example 16 is a system comprising: a heart sound input circuit configured to: receive a first signal including heart sound information from a first axis over a first physiologic interval; and receive a second signal including heart sound information from a second axis over the first physiologic interval, the first physiologic interval including at least a portion of a cardiac cycle, the first axis different than the second axis; and a heart sound circuit configured to produce a composite heart sound signal over the first physiologic interval using the first and second signals.

In Example 17, the subject matter of Example 16 may optionally be configured such that the heart sound circuit is configured to correct the first signal over the first physiologic interval using the second signal over the first physiologic interval.

In Example 18, the subject matter of any one or more of Examples 6-17 may optionally be configured such that the heart sound circuit is configured to produce the composite heart sound signal using the first and second signals without reference to an electrical signal of the heart.

In Example 19, the subject matter of any one or more of Examples 16-18 may optionally be configured such that the heart sound input circuit is configured to receive a third signal including heart sound information from a third axis over the first physiologic interval, the third axis different than the first and second axes.

In Example 20, the subject matter of Example 19 may optionally be configured such that the heart sound circuit is configured to produce a plurality of potential composite heart sound signals as a function of the first and second signals and to produce the composite heart sound signal by selecting the potential composite heart sound signal using a signal-to-noise-ratio of the potential composite heart sound signals.

In Example 21, the subject matter of Example 20 may optionally be configured such that the heart sound circuit is configured to produce each of the potential composite heart sound signals by applying a plurality of first coefficients to the first signal, a plurality of second coefficients to the second signal, and a plurality of third coefficients to the third signal.

In Example 22, the subject matter of Example 21 may optionally be configured such that the heart sound circuit is configured to select the first and second coefficients using the first and second signals over the first physiologic interval, and wherein the heart sound circuit is configured to apply the selected first coefficient to the first signal and the second coefficient to the second signal to produce the composite heart sound signal over a second physiologic interval subsequent to the first physiologic interval.

Example 23 is a method comprising: receiving a first signal including heart sound information from a first axis over a first physiologic interval using a heart sound input circuit: receiving a second signal including heart sound information from a second axis over the first physiologic interval, the first physiologic interval including at least a portion of a cardiac cycle, the first axis different than the second axis; and producing, using a heart sound circuit, a composite heart sound signal over the first physiologic interval using the first and second signals.

In Example 24, the subject matter of Example 23 may optionally be configured such that producing the composite heart sound signal includes correcting the first signal over the first physiologic interval using the second signal over the first physiologic interval.

In Example 25, the subject matter of any one or more of Examples 23-24 may optionally be configured such that producing the composite heart sound signal includes using the first and second signals without reference to an electrical signal of the heart.

In Example 26, the subject matter of any one or more of Examples 23-25 may optionally include receiving a third signal including heart sound information from a third axis over the first physiologic interval using the heart sound input circuit, the third axis different than the first and second axes.

In Example 27, the subject matter of any one or more of Examples 23-26 may optionally include producing, using the heart sound circuit, a plurality of potential composite heart sound signals using the first and second signals; wherein producing the composite heart sound signal includes selecting the potential composite heart sound signal using a signal-to-noise-ratio of the potential composite heart sound signals.

In Example 28, the subject matter of any one or more of Examples 26-27 may optionally include wherein producing each of the potential composite heart sound signals includes applying a plurality of first coefficients to the first signal, a plurality of second coefficients to the second signal, and a plurality of third coefficients to the third signal using the heart sound circuit.

In Example 29, the subject matter of Example 28 may optionally include selecting the first and second coefficients using the first and second signals over the first physiologic interval; and applying the selected first and second coefficients to the first signal and the second signal to produce the composite heart sound signal over a second physiologic interval subsequent to the first physiologic interval.

In Example 30, the subject matter of any one or more of Examples 23-29 may optionally include detecting the first signal from the first axis and the second signal from the second axis using a multi-axis heart sound sensor.

Example 31 is a system comprising: at least one heart sound sensor configured to: detect a first signal including heart sound information from a first axis over a first physiologic interval; and detect a second signal including heart sound information from a second axis over the first physiologic interval, the first physiologic interval including at least a portion of a cardiac cycle, the first axis different than the second axis.

In Example 32, the subject matter of Example 31 may optionally be configured such that the at least one heart sound sensor is configured to produce a third signal including heart sound information from a third axis over the first physiologic interval, the third axis different than the first and second axes.

In Example 33, the subject matter of Example 32 may optionally be configured such that the heart sound circuit is configured to produce the composite heart sound signal over the first physiologic interval using the first, second, and third signals.

In Example 34, the subject matter of any one or more of Examples 32-33 may optionally be configured such that the heart sound circuit is configured to produce a plurality of potential composite heart sound signals by applying a plurality of first coefficients to the first signal, a plurality of second coefficients to the second signal, and a plurality of third coefficients to the third signal, and wherein the heart sound circuit is configured to produce the composite heart sound signal by selecting the potential composite heart sound signal using a signal-to-noise-ratio of the potential composite heart sound signals.

In Example 35, the subject matter of any one or more of Examples 31-34 may optionally be configured such that the heart sound circuit is configured to store the first and second coefficients based on a condition sensed by the heart sound circuit, and is configured to apply the first and second coefficients when the condition is sensed again.

An example (e.g., "Example 36") of subject matter (e.g., a system or apparatus) may optionally combine any portion or combination of any portion of any one or more of Examples 1-35 to include "means for" performing any portion of any one or more of the functions or methods of Examples 1-35, or a "machine-readable medium" (e.g., massed, non-transitory, etc.) including instructions that, when performed by a machine, cause the machine to perform any portion of any one or more of the functions or methods of Examples 1-35.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 illustrates a table of example coefficients that can be applied to signals including heart sound information to produce a composite signal.

DETAILED DESCRIPTION

Figure 1A:
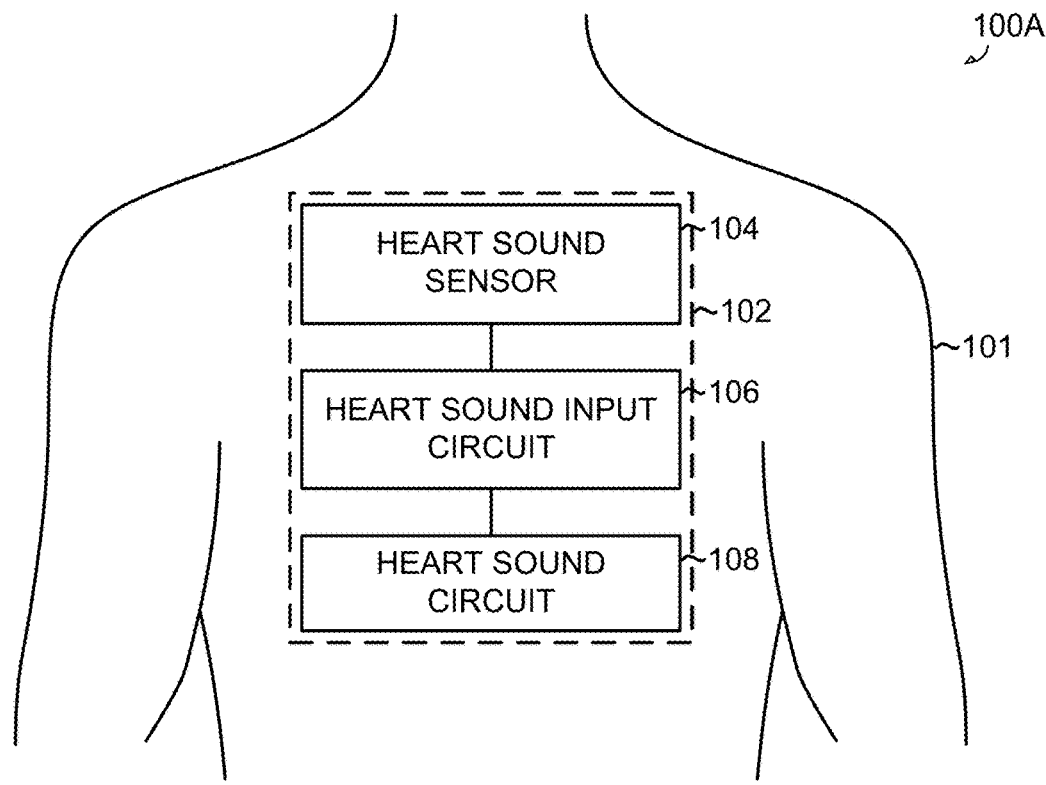
FIG. 1A-1B illustrate schematic views of example cardiac monitoring systems.

Heart sounds are recurring mechanical signals associated with cardiac vibrations from and blood flow through the heart with each cardiac cycle, and can be separated and classified according to activity associated with the vibrations and blood flow. The first heart sound (S1) is the vibrational sound made by the heart during closure of the atrioventricular (AV) valves. The second heart sound (S2) is the beginning of diastole, and is made by the aortic and pulmonary valves. The third and fourth heart sounds (S3, S4) are related to filling pressures of the left ventricle during diastole.

Heart sounds can be sensed or detected by sensors, such as accelerometers, in proximity to a heart. However, sensors used to detect heart sounds often detect other vibrations resulting in signal noise. The noise can be caused by, among other things, postural changes, body movement, changes in orientation relative to the direction of gravity, etc. Electrical signal characteristics, such as an R wave or other marker or fiducial of an electrocardiogram (ECG) signal, can be used to reduce signal noise in a heart sound signal, such as during heart sound detection or averaging (e.g., ensemble averaging), for example, to lower a signal-to-noise ratio or increase alignment between features across a number of cardiac cycles. However, reliance on electrical signal characteristics may increase the complexity, cost, or power consumption of a device configured to sense or detect heart sounds. The present inventors have recognized, among other things, that multiple heart sound signals, in certain examples, without reference to an electrical signal characteristic, can be used to create a composite heart sound signal with a signal-to-noise ratio relatively lower than a single heart sound signal. Because the composite heart sound signal is not reliant on an R wave or other marker or fiducial of an ECG signal, it is not susceptible to errors in the electrical signal characteristic. Because components required to produce the R wave signal or other electrical signal characteristic are not required, a medical device configured to detect heart sounds can be manufactured in a smaller form factor, lowering bill of material (BOM) expense of the device. Elimination of such components can also reduce required power consumption of the device, increasing efficiency and therefore improving battery life of the device.

In some examples, multiple signals including heart sound information a first physiologic interval can be used to produce a composite heart sound signal over the first physiologic interval using a heart sound circuit. In some examples, these signals can be provided by a multi-axis accelerometer. In one example, multiple heart sound signals can be combined using coefficients applied to each of the individual heart sound signals to create a composite heart sound signal. Selection of coefficients can be selected based on a comparison of multiple possible composite signals. The coefficients selected can be used after selection through multiple physiologic intervals and can be reselected when a change in posture, position relative to the direction of gravity, or other change is detected. These processes can reduce the signal-to-noise ratio of a heart sound signal produced by a device, increasing route mean square (RMS) power of the signal, which may therefor reduce the need for amplification and filtering. Because of this, a required processing power can be reduced, further increasing operating efficiency and improving battery life of the device.

FIG. 1A illustrates a schematic view of an example system 100A including a device 102 configured to receive heart sound information of a patient 101, and to provide a composite heart sound signal. In certain examples, the device 102 can include an ambulatory medical device (AMD), including an implantable medical device (IMD), such as a leadless, implantable, or insertable cardiac monitor, pacemaker, or defibrillator, an external or wearable device or remote patient monitor, or one or more other management or therapy devices configured to detect or receive heart sound information of the patient 101. In an example, the device 102 can include a heart sound sensor 104 configured to receive heart sound information of a heart of the patient 101. The device 102 can also include a heart sound input circuit 106 configured to receive heart sound signals from the heart sound sensor 104. A heart sound circuit 108 can be configured to produce a composite heart sound signal using the signals including heart sound information that are received from the heart sound input circuit 106.

In some examples, the heart sound sensor 104 can be a sensor configured to detect heart sound information along one or more axes during physiologic intervals that include at least a portion of a cardiac cycle. The heart sensor 104 can be further configured to produce one or more signals as a function of the detected heart sound information. In some examples, the heart sound sensor 104 can be an accelerometer, microphone, or other transducer configured to produce an electronic signal based on a detected force, acceleration, or pressure.

In some examples, the heart sound input circuit 106 can be an electronic circuit or series of circuits configured to receive, modify, and transmit heart sound signals supplied by the heart sound sensor 104. In some examples, the heart sound circuit 108 can be an electronic circuit or series of circuits configured to receive and process signals received from the heart sound input circuit 106. In some examples, the heart sound circuit 108 can be configured to perform multiple operations (or calculations) on or using the signals received from the heart sound input circuit 106 to produce a composite signal.

In operation of one example, the heart sound sensor 104 can detect heart sound information of a heart of the patient 101 over one or more physiologic intervals that include at least a portion of a cardiac cycle. The heart sound sensor 104 can then transmit one or more signals containing heart sound information to the heart sound input circuit 106. The heart sound input circuit 106 can modify the one or more signals containing heart sound information, in some examples, and can transmit the signal(s) to the heart sound circuit 108. The heart sound circuit 108 can perform analysis or operations on the signal or signals provided by the heart sound input circuit 106 to produce a composite heart sound signal, as discussed below in further detail. In some examples, because heart sound detection of the system 100 does not rely on electrical heart signals, the produced composite heart sound signal can be less susceptible to electric or electromagnetic interference than systems requiring use of electrical heart signals, such as an ECG signal.

Figure 1B:
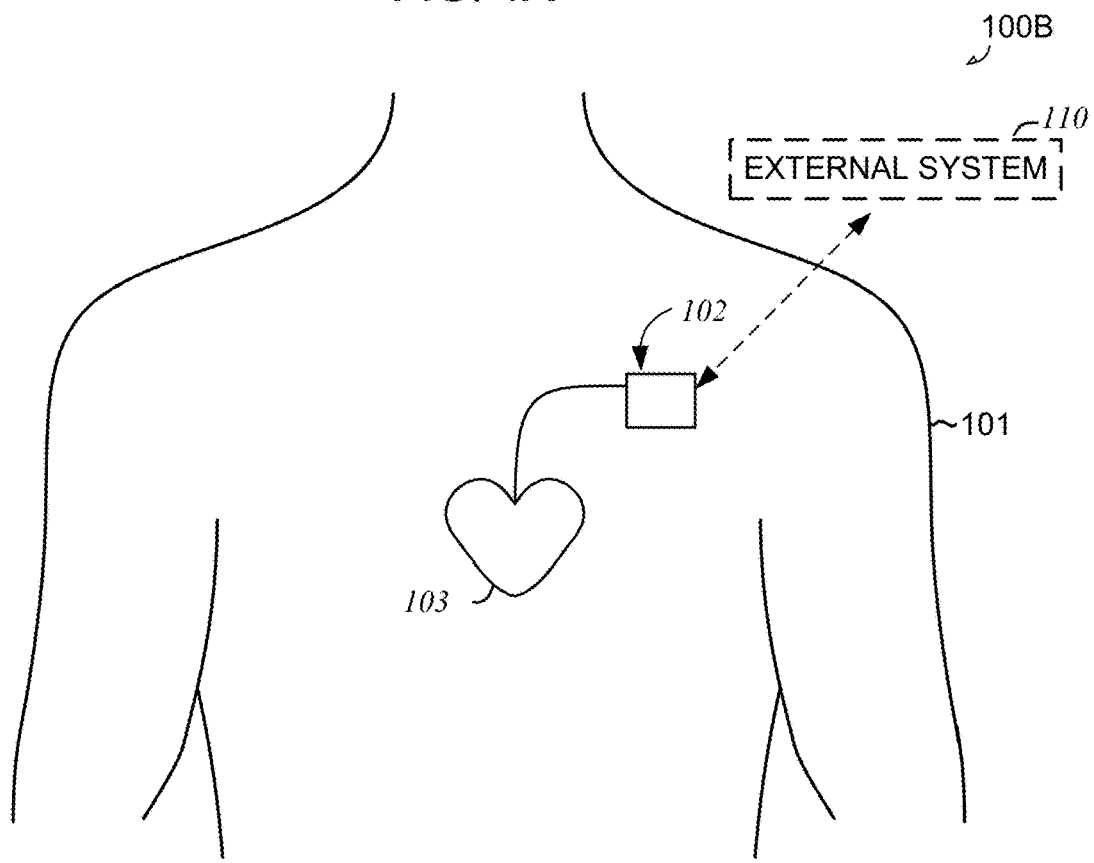

FIG. 1B illustrates a schematic view of a system 100B including a device 102 configured to detect heart sound information of a heart 103 of patient the 101, and an external system 110.

In some examples, the external system 110 can be a device located external to the patient 101, such as in a portable computer, wearable device, or other device station. The external system 110 can include one or more of the components of the device 102, such as the heart sound sensor 104, the heart sound input circuit 106, and the heart sound circuit 108. In some examples, the external system 110 can be in wired or wireless communication with the device 102, depending on system design and requirements.

Figure 2:
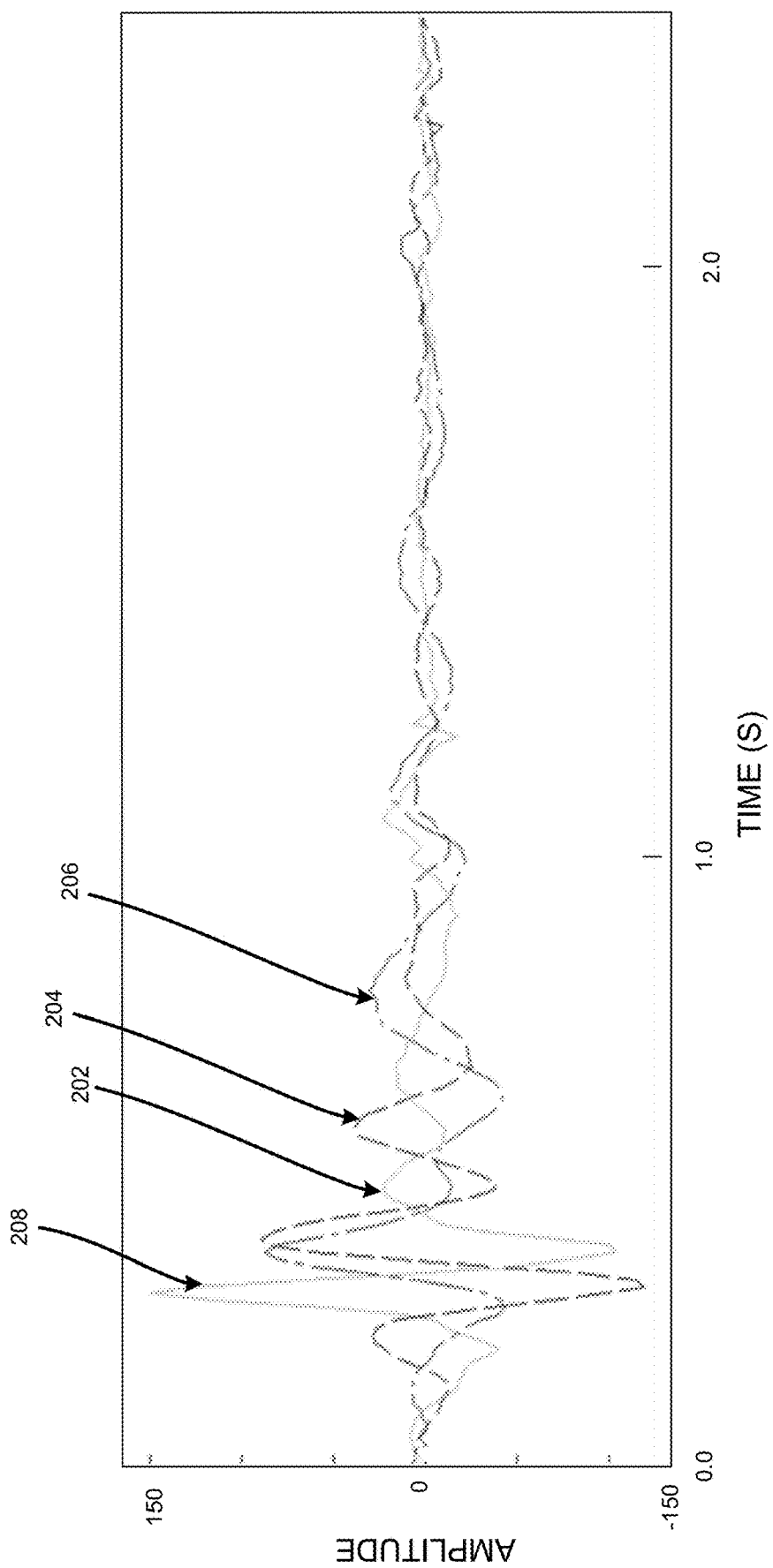
FIG. 2 illustrate a graph of example signals including heart sound information provided by an example system over a physiologic interval.

FIG. 2 illustrate a graph of signals containing heart sound information detected over a physiologic interval, including a first signal 202, a second signal 204, and a third signal 206. The first signal 202 can include heart sound information over a first physiologic interval. In an example, the first signal 202 can include heart sound information detected along a first axis. The second signal 204 can include heart sound information over the first physiologic interval. In an example, the second signal 204 can include heart sound information detected along a second axis. The third signal 206 can include heart sound information over the first physiologic interval. In an example, the third signal 206 can include heart sound information detected along a third axis. In some examples, the first, second, and third axes can all be different from each other. In an example, an input circuit and a heart sound circuit, such as the input circuit 106 and the heart sound circuit 108 of FIG. 1, can correct the heart sound signals 202, and/or 204, and/or 206 to produce a composite heart sound signal. In other examples, only two of the signals 202, 204, and 206 can be detected and used to produce the composite signal.

In one example, each of the signals 202, 204, and 206 can be aligned in the time domain for analysis. In some examples, one of the signals 202, 204, and 206 can be inverted or can have another defect (such as excessive noise, etc.). In the example shown in FIG. 2, the first signal 202 includes a peak amplitude 208, which can be a specific heart sound fiducial (e.g. S1, S2, S3, etc.), that is out of phase with similar fiducials of the second and third signals 204 and 206, indicating that the first signal 202 is out of phase with the second signal 204 and the third signal 206, In this example, it may be desirable to invert the first signal 202 to align the first signal 202 with the second and third signals 204 and 206. Alignment, correction, or creation of a composite signal can be performed in several ways. In one example, the first signal 202 can be aligned with the second and third signals 204 and 206 by applying one or more coefficients to the first, second, and third signals 202, 204, and 206, as discussed further below with respect to FIG. 3.

FIG. 3 illustrates a table of example coefficients that can be applied to signals including heart sound information to produce a composite signal. When forming a single, composite signal, there are many ways the signals can be used to create a composite signal. In some examples, the heart sound circuit can be configured to produce a plurality of potential composite heart sound signals as a function of the first and second signals and can be further configured to produce the composite heart sound signal by selecting the potential composite heart sound signal using a signal-to-noise-ratio of the potential composite heart sound signals. In one further example, the heart sound circuit can be configured to produce each of the potential composite heart sound signals by applying a plurality of first coefficients to the first signal, a plurality of second coefficients to the second signal, and a plurality of third coefficients to the third signal. The potential composite signal with the highest RMS power, lowest signal-to-noise ratio, or other quality can be selected as the composite signal.

In one example, the following equation can be used, where the first signal is represented by A, the second signal is represented by B, the third signal is represented by C, and the composite signal is represented by V.

$$V = A*X + B*Y + C*Z \quad (1)$$

Coefficients X, Y, and Z, of Equation 1 above, can be applied to each of the signals. In some examples, multiple coefficients can be used, resulting in multiple potential composite signals, V. Each of the composite signals V can be compared to each of the other composite signals V, for example, by calculating, for example, the RMS power of each of the composite signals V. Then, the composite signal V having the highest RMS power can be selected.

In one example, three coefficients, −1, 0, and 1 can be used as coefficients X, Y, and Z, resulting in 27 combinations or 27 composite signals V. However, only thirteen of the combinations of this example are unique, as shown in FIG. 3. Each of the thirteen combinations can be applied using Equation 1. For example, the first combination can be applied, as shown in Equation 2, below.

$$Z_1 = A*1 + B*0 + C*0 \quad (2)$$

This solution results in elimination of the second and third signals B and C, making $Z_1 = A$. That is, the first composite signal is equal to the first signal in the first potential solution.

Each of the solutions can be similarly calculated. For example, the eleventh solution can be calculated, as shown in Equation 3 below.

$$Z_{11} = A*-1 + B*1 + C*1 \quad (3)$$

The eleventh solution shown in Equation 3 inverts the first signal relative to the second and third signals. Applying this solution to the example illustrated in FIG. 2 results in inverting the first signal 202 relative to the second signal 204 and the third signal 206, substantially aligning the first, second, and third signals 202, 204, and 206. This solution will have the highest RMS power of any of the thirteen solutions and can therefore be selected as the best of the thirteen possible solutions of the composite signal. Though the example below is discussed with respect to coefficients of −1, 0, and 1, other coefficients can be used.

In some other examples, the composite signals can be analyzed in other ways to determine the best solution. For example RMS power for each solution can be calculated at multiple heart sound fiducials such as S1, S2, S3, etc. (or other fiducials). The RMS power at individual fiducials for each solution can be compared to determine the best solution or composite signal.

In another example, the signal-to-noise ratio for each solution can be calculated and each solution (or potential composite signal) can be compared to determine the potential composite signal having the lowest signal-to-noise ratio. The potential composite signal with the lowest signal-to-noise ratio can then be selected as the composite signal.

Once a solution (and therefore composite signal) is selected, the coefficients for that solution can be selected (or stored) and applied to additional physiologic intervals to obtain composite signals for subsequent physiologic intervals. When a change in conditions is detected, the coefficients can be recalculated or reselected using on or more of the processes described herein.

In some examples, coefficients can be stored for each posture (or other condition that may affect the signals, such as movement) and the coefficients for each posture can be applied when it is determined that the same posture (or other condition) as being appropriate for the postural condition. In other examples, the stored coefficients can be confirmed as being optimal for the detected posture or condition. In other examples, the coefficients can be updated when the coefficients are determined to be sub-optimal. In another example, the stored coefficients can periodically updated at predetermined intervals. For example, the coefficients can be updated every third, fourth, fifth, tenth, and the like time the condition or posture is detected.

Though the solutions are discussed above with respect to three signals, two signals can also be used to produce a composite signal in other examples. For example, the heart sound circuit can be configured to correct the first signal over the first physiologic interval using the second signal over the first physiologic interval. And, similarly, the heart sound circuit can be configured to correct the second signal over the first physiologic interval using the first signal over the first physiologic interval. In either example, the heart sound circuit can be configured to produce a plurality of potential composite heart sound signals as a function of the first and second signals and to produce the composite heart sound signal by selecting the potential composite heart sound signal using a signal-to-noise-ratio of the potential composite heart sound signals. In some examples, the first and second signals can be changed relative to each other and the RMS power, signal-to-noise ratio, or other characteristic of the composite signal can be calculated to select a composite signal.

In another example, the heart sound circuit can be configured to select first and second coefficients using the first and second signals over the first physiologic interval, and the heart sound circuit can be configured to apply the selected first coefficient to the first signal and the second coefficient to the second signal to produce the composite heart sound signal over a second physiologic interval subsequent to the first physiologic interval. The composite signal can be used for multiple or many subsequent physiologic intervals, until, for example, a change in condition (change in posture, etc.) is detected.

Figure 4:
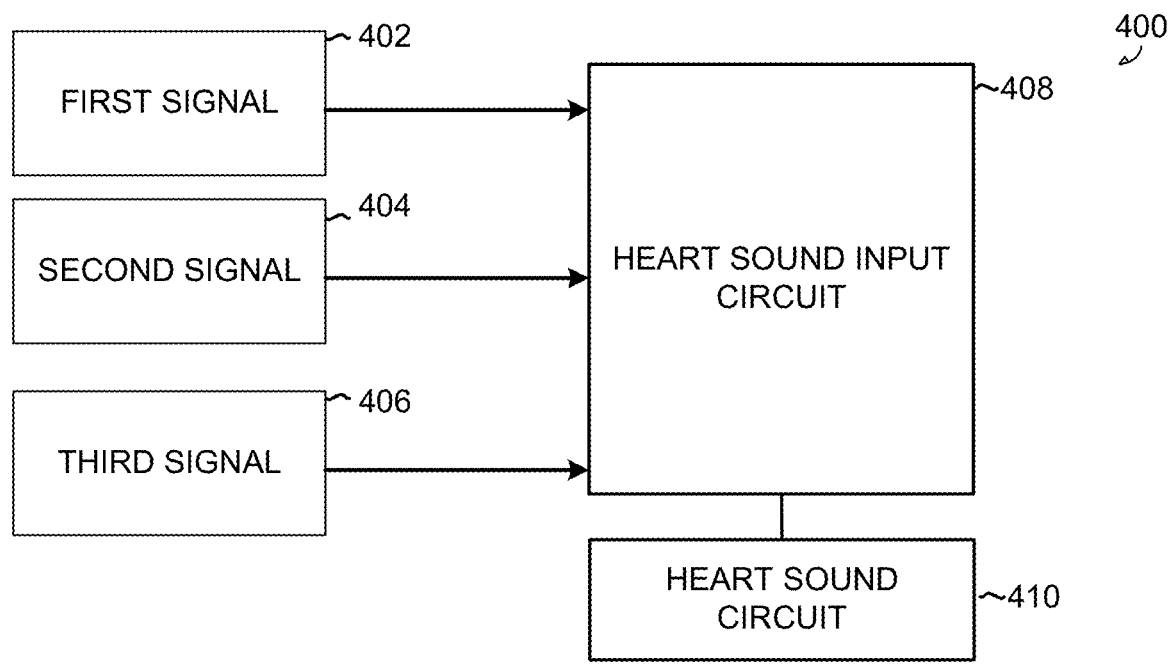
FIG. 4 illustrates a schematic view of an example system including a heart sound input circuit and a heart sound circuit.

FIG. 4 illustrates a schematic view of example system 400 including a heart sound input circuit 408 and a heart sound circuit 410. FIG. 4 also illustrates a first signal 402, a second signal 404, and a third signal 406. The heart sound input circuit 408 can receive the first signal 402, the second signal 404, and the third signal 406, in some examples. The heart sound input circuit 408 can provide one or more of the first signal 402, the second signal 404, and the third signal 406 to the heart sound circuit 410 for correction or creation of a composite. In some examples, the heart sound input circuit 408 can modify one or more of the first signal 402, the second signal 404, and the third signal 406 before providing the signals to the heart sound circuit 410.

In some examples, a heart sound sensor, such as the heart sound sensor 104 of FIG. 1, can produce each of the first signal 402, the second signal 404, and the third signal 406. In one example, the heart sound sensor can produce the first signal 402, where the first signal 402 can include heart sound information detected along a first axis. In the same example, the heart sound sensor can produce the second signal 404, where the second signal 404 can include heart sound information taken along a second axis different than the first axis. In another example, multiple, single-axis sensors can produce the first signal 402 and the second signal 404.

In either of these examples, the heart sound input circuit 408 can receive the first signal 402 and the second signal 404, which can provide the first signal 402 and the second signal 404 to the heart sound circuit 410. The heart sound circuit 410 can then combine the first signal 402 and the second signal 404 to produce a composite heart sound signal. The heart sound circuit 410 can create the composite heart sound signal by trying multiple solutions of combinations of the first signal 402 and the second signal 404 and can select the solution or composite signal with the highest RMS power, lowest signal-to-noise ratio, or either of these at any heart sound fiducial, among other ways, as discussed in the examples above with respect to FIG. 3.

In some other examples, the heart sound circuit 410 can use the first signal 402, the second signal 404, and the third signal 406 to produce the composite heart sound signal. In one of these examples, a single sensor can produce the first signal 402 based on detected heart sound information along a first axis, the second signal 404 based on detected heart sound information along a second axis different than the first axis, and the third signal 406 based on detected heart sound information along a third axis different than the first and second axes.

In another of these examples, multiple sensors can be used to produce the first signal 402, the second signal 404, and the third signal 406. For example, a first sensor can produce the first signal 402 based on detected heart sound information along a first axis, a second sensor can produced the second signal 404 based on detected heart sound information along a second axis different than the first axis, and a third sensor can produce the third signal 406 based on detected heart sound information along a third axis different than the first and second axes. The first, second, and third signals 402, 404, and 406 can then be analyzed and used to create a composite signal as discussed above in other examples.

In any of the examples discussed above, the composite heart sound signal, an averaged composite heart sound signal, or a composite heart sound signal ensemble over multiple physiologic intervals can be used to detect S1, S2, S3, or a calculation of one or more windows or markers used to detect or determine S3 (e.g., using S2 timing, etc.). These methods, devices, and systems can therefore be used to detect heart sounds or heart sound fiducials over one or more physiologic intervals and can be used to produce a composite heart sound signal without the aid of a detected R wave or other marker or fiducial of an electrical signal of the heart. Because an R wave signal is not required to produce a composite heart sound signal, electrical error and electromagnetic interference can be reduced. Additionally, by using multiple signals to create a composite heart sound signal, signal-to-noise ratio of the composite heart sound signal can be reduced relative to use of a single signal R wave signal or a single heart sound signal.

In other examples, more sensors can be used. For example, two multi-axis sensors can be used and multiple composite heart sound signals can be averaged or compared and the better signal selected. Alternatively two single-axis sensors can be used at each axis and the single-axis signals can be averaged (or the better signal selected) prior to combination.

Figure 5:
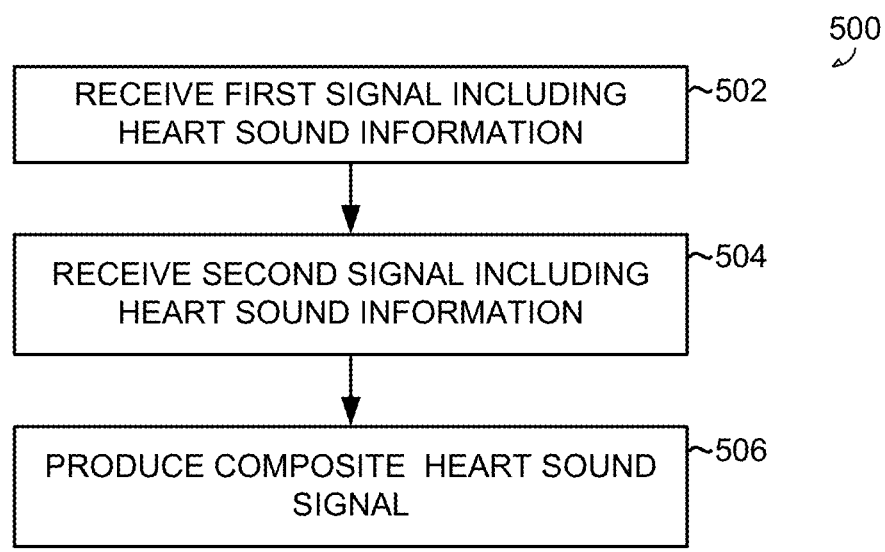
FIG. 5 illustrates an example method of producing a composite heart sound signal.

FIG. 5 illustrates an example method 500 of producing a composite heart sound signal. The steps or operations of method 500 are illustrated in a particular order for convenience and clarity; some of the discussed operations can be performed in a different sequence or in parallel without materially impacting other operations.

At step 502, a first signal including heart sound information over a first physiologic interval can be received, such as using a heart sound input circuit (e.g., heart sound input circuit 408 of FIG. 3, etc.). In one example, a first signal including heart sound information from a first axis over a first physiologic interval can be received using the heart sound input circuit. At step 504, a second signal including heart sound information over the first physiologic interval can be received, such as using the heart sound input circuit, in one example, a second signal including heart sound information from a second axis over the first physiologic interval using the heart sound input circuit, where the first physiologic interval including at least a portion of a cardiac cycle and where the first axis different than the second axis. In an example, a heart sound sensor, such as the heart sound sensor 104 of FIG. 1, can produce the first and second heart sound signals. In other examples, the second heart sound signal can be produced by a second, different heart sound sensor.

At step 506 a heart sound circuit, such as the heart sound circuit 410 of FIG. 4, can produce a composite heart sound signal over the first physiologic interval using the first and second signals. In this way, the composite signal can be produced using the first and second signals without reference to an electrical signal of the heart. In one example, the composite heart sound signal can be produced by correcting the first signal over the first physiologic interval using the second signal over the first physiologic interval.

In another example, the heart sound input circuit can receive a third signal including heart sound information from a third axis over the first physiologic interval using, where the third axis different than the first and second axes. In some of these examples, the heart sound circuit can produce a plurality of potential composite heart sound signals using the first and second signals. The composite heart sound signal can be produced by selecting the potential composite heart sound signal using a signal-to-noise-ratio of the potential composite heart sound signals. For example, the potential composite heart sound signal with the lowest signal-to-noise ratio can be selected to be the composite signal. In another example, the composite heart sound signal can be produced by selecting the potential composite heart sound signal using a RMS power of the potential composite heart sound signals. For example, the potential composite heart sound signal with highest RMS power can be selected to be the composite signal.

In some of these examples, the heart sound circuit can produce each of the potential composite heart sound signals by applying a plurality of first coefficients to the first signal, a plurality of second coefficients to the second signal, and a plurality of third coefficients to the third signal using the heart sound circuit. The heart sound circuit can then select the potential composite heart sound signal, for example, with the highest RMS power or lowest signal-to-noise ratio, etc.

In another example, the first and second coefficients can be selected using the first and second signals over the first physiologic interval and the coefficients can be applied to the first signal and the second signal to produce the composite heart sound signal over a second physiologic interval subsequent to the first physiologic interval. In other examples, the coefficients can be applied to produce the composite heart sound signal over many subsequent physiologic intervals, for example, until a change in condition (such as posture or orientation relative to the direction of gravity) is detected.

In another example, the first signal can be detected from the first axis and the second signal can be detected from the second axis using a multi-axis heart sound sensor. In another example, the multi-axis heart sound sensor can also detect a third signal from a third axis.

Figure 6:
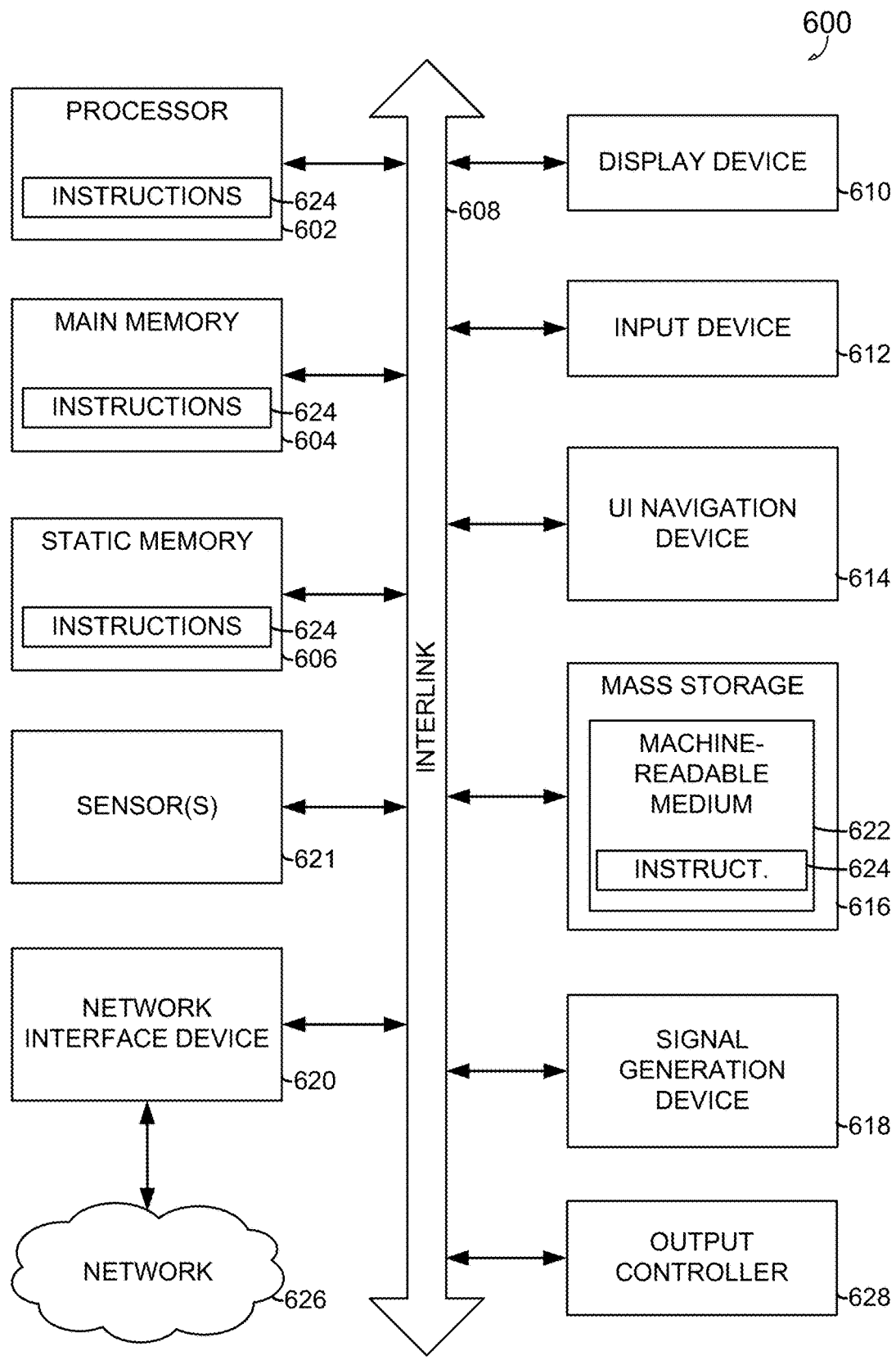
FIG. 6 illustrates a block diagram of an example machine upon which any one or more of the techniques (e.g., methodologies) discussed herein may perform.

FIG. 6 illustrates a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof, either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A system comprising:
   a heart sound input circuit configured to:
      receive a first signal including heart sound information from a first axis over a first physiologic interval; and
      receive a second signal including heart sound information from a second axis over the first physiologic interval, the first physiologic interval including at least a portion of a cardiac cycle, the first axis different than the second axis; and
   a heart sound circuit configured to:
      correct the first signal over the first physiologic interval using the second signal over the first physiologic interval; and
      produce a composite heart sound signal over the first physiologic interval using the first and second signals.

2. The system of claim 1, wherein the heart sound circuit is configured to produce the composite heart sound signal using the first and second signals without reference to an electrical signal of the heart.

3. The system of claim 1, wherein the heart sound input circuit is configured to receive a third signal including heart sound information from a third axis over the first physiologic interval, the third axis different than the first and second axes.

4. The system of claim 3, wherein the heart sound circuit is configured to produce a plurality of potential composite heart sound signals as a function of the first and second signals, and
wherein the heart sound circuit is configured to produce the composite heart sound signal by selecting one of the plurality of potential composite heart sound signal using a signal-to-noise-ratio of each of the plurality potential composite heart sound signals.

5. The system of claim 4, wherein the heart sound circuit is configured to produce each of the potential composite heart sound signals by applying a plurality of first coefficients to the first signal, a plurality of second coefficients to the second signal, and a plurality of third coefficients to the third signal.

6. The system of claim 5, wherein the heart sound circuit is configured to select the first and second coefficients using the first and second signals over the first physiologic interval, and wherein the heart sound circuit is configured to apply the selected first coefficient to the first signal and the second coefficient to the second signal to produce the composite heart sound signal over a second physiologic interval subsequent to the first physiologic interval.

7. The system of claim 1, wherein to correct the first signal over the first physiologic interval, the heart sound circuit is configured to select or invert the first signal over the first physiologic interval using the second signal over the first physiologic interval.

8. The system of claim 1, wherein to correct the first signal over the first physiologic interval, the heart sound circuit is configured to invert the first signal over the first physiologic interval using the second signal over the first physiologic interval.

9. A method comprising:
receiving a first signal including heart sound information from a first axis over a first physiologic interval using a heart sound input circuit;
receiving a second signal including heart sound information from a second axis over the first physiologic interval, the first physiologic interval including at least a portion of a cardiac cycle, the first axis different than the second axis; and
producing, using a heart sound circuit, a composite heart sound signal over the first physiologic interval using the first and second signals,
wherein producing the composite heart sound signal includes correcting the first signal over the first physiologic interval using the second signal over the first physiologic interval.

10. The method of claim 9, wherein producing the composite heart sound signal includes using the first and second signals without reference to an electrical signal of the heart.

11. The method of claim 9, further comprising:
receiving a third signal including heart sound information from a third axis over the first physiologic interval using the heart sound input circuit, the third axis different than the first and second axes.

12. The method of claim 9, further comprising:
producing, using the heart sound circuit, a plurality of potential composite heart sound signals using the first and second signals; wherein producing the composite heart sound signal includes selecting one of the plurality potential composite heart sound signal using a signal-to-noise-ratio of the potential composite heart sound signals.

13. The method of claim 12, wherein producing each of the potential composite heart sound signals includes applying a plurality of first coefficients to the first signal, a plurality of second coefficients to the second signal, and a plurality of third coefficients to a third signal using the heart sound circuit.

14. The method of claim 13, further comprising:
selecting the first and second coefficients using the first and second signals over the first physiologic interval; and
applying the selected first and second coefficients to the first signal and the second signal to produce the composite heart sound signal over a second physiologic interval subsequent to the first physiologic interval.

15. The method of claim 9, further comprising:
detecting the first signal from the first axis and the second signal from the second axis using a multi-axis heart sound sensor.

16. The method of claim 9, wherein correcting the first signal over the first physiologic interval comprises selecting or inverting the first signal over the first physiologic interval using the second signal over the first physiologic interval.

17. The method of claim 9, wherein correcting the first signal over the first physiologic interval comprises inverting the first signal over the first physiologic interval using the second signal over the first physiologic interval.

18. A system comprising:
means for receiving a first signal including heart sound information from a first axis over a first physiologic interval and a second signal including heart sound information from a second axis over the first physiologic interval, the first physiologic interval including at least a portion of a cardiac cycle, the first axis different than the second axis; and
means for correcting the first signal over the first physiologic interval using the second signal over the first physiologic interval and producing a composite heart sound signal over the first physiologic interval using the corrected first signal.

19. The system of claim 18, comprising:
at least one heart sound sensor configured to:
detect a first signal including heart sound information from a first axis over a first physiologic interval;
detect a second signal including heart sound information from a second axis over the first physiologic interval, the first physiologic interval including at least a portion of a cardiac cycle, the first axis different than the second axis; and
detect a third signal including heart sound information from a third axis over the first physiologic interval, the third axis different than the first and second axes;
wherein the means for receiving the first and second signals comprise a heart sound input circuit configured to receive the first, second, and third signals; and
wherein the means for correcting the first signal comprises a heart sound circuit configured to produce a plurality of potential composite heart sound signals over the first physiologic interval using the first, second, and third signals, and to select a composite heart sound signal from the plurality of potential composite heart sound signals using a signal-to-noise-ratio of the plurality of potential composite heart sound signals,
wherein to produce the plurality of potential composite heart sound signals, the heart sound circuit is configured to:
apply a plurality of first coefficients to the first signal;
apply a plurality of second coefficients to the second signal; and
apply a plurality of third coefficients to the third signal.

20. The system of claim 19, wherein the heart sound circuit is configured to:
- produce the composite heart sound signal over the first physiologic interval using the first, second, and third signals;
- store the first and second coefficients based on a condition sensed by the heart sound circuit; and
- apply the first and second coefficients when the condition is sensed again.

* * * * *